United States Patent [19]
Fujioka et al.

[11] Patent Number: 6,056,732
[45] Date of Patent: *May 2, 2000

[54] DISPOSABLE DIAPER

[75] Inventors: Yoshihisa Fujioka, Kagawa; Rumi Yamaki; Yoshio Ono, both of Ehime, all of Japan

[73] Assignee: Uni-Charm Corporation, Ehime, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/908,253

[22] Filed: Aug. 7, 1997

[30] Foreign Application Priority Data

Aug. 19, 1996 [JP] Japan .................................. 8-217377
Nov. 19, 1996 [JP] Japan .................................. 8-308108
Dec. 26, 1996 [JP] Japan .................................. 8-348465

[51] Int. Cl.⁷ ...................................................... A61F 13/15
[52] U.S. Cl. ................................... 604/385.1; 604/385.2; 604/386; 604/389; 604/391
[58] Field of Search ........................... 604/385.1, 385.2, 604/386, 389, 390, 391

[56] References Cited

U.S. PATENT DOCUMENTS

| | | | |
|---|---|---|---|
| 4,059,114 | 11/1977 | Richards | 604/370 |
| 4,253,461 | 3/1981 | Strickland | 604/385.2 |
| 4,351,340 | 9/1982 | McLeod . | |
| 4,680,030 | 7/1987 | Coates et al. . | |
| 4,775,375 | 10/1988 | Aledo . | |
| 4,820,296 | 4/1989 | Masliyah | 604/389 |
| 4,826,499 | 5/1989 | Ahr | 604/385.2 |
| 4,850,988 | 7/1989 | Aledo | 604/385.1 |
| 4,850,992 | 7/1989 | Amaral et al. | 604/385.1 |
| 4,911,702 | 3/1990 | O'Leary et al. . | |
| 5,275,588 | 1/1994 | Matsumoto et al. | 604/390 |
| 5,382,246 | 1/1995 | Kawano . | |
| 5,531,731 | 7/1996 | Brusky | 604/390 |

FOREIGN PATENT DOCUMENTS

| | | |
|---|---|---|
| 0641552A1 | 3/1995 | European Pat. Off. . |
| 0758543A1 | 2/1997 | European Pat. Off. . |
| 284623 | 2/1990 | Japan . |
| 2080093 | 2/1982 | United Kingdom . |
| 2262873 | 7/1993 | United Kingdom . |
| WO 90/04374 | 5/1990 | WIPO . |
| WO 91/09580 | 7/1991 | WIPO . |
| WO 95/06451 | 3/1995 | WIPO . |

OTHER PUBLICATIONS

Translation of Stary DE 3205931.

*Primary Examiner*—Mark O. Polutta
*Attorney, Agent, or Firm*—Koda & Androlia

[57] ABSTRACT

A well-fitting disposable diaper having a front gathering to be applied to the crotch of a wearer. The front gathering is formed by elastic members disposed about a border between a crotch region and a front waist region of the diaper and includes one end portions of first and second thin parts which are disposed in the crotch region and the front waist region, respectively. Because the first thin parts are elongated between the second thin parts in the front gathering, the front gathering can readily shrink to press the crotch of a wearer or a protector against incontinence to be applied thereto.

4 Claims, 6 Drawing Sheets

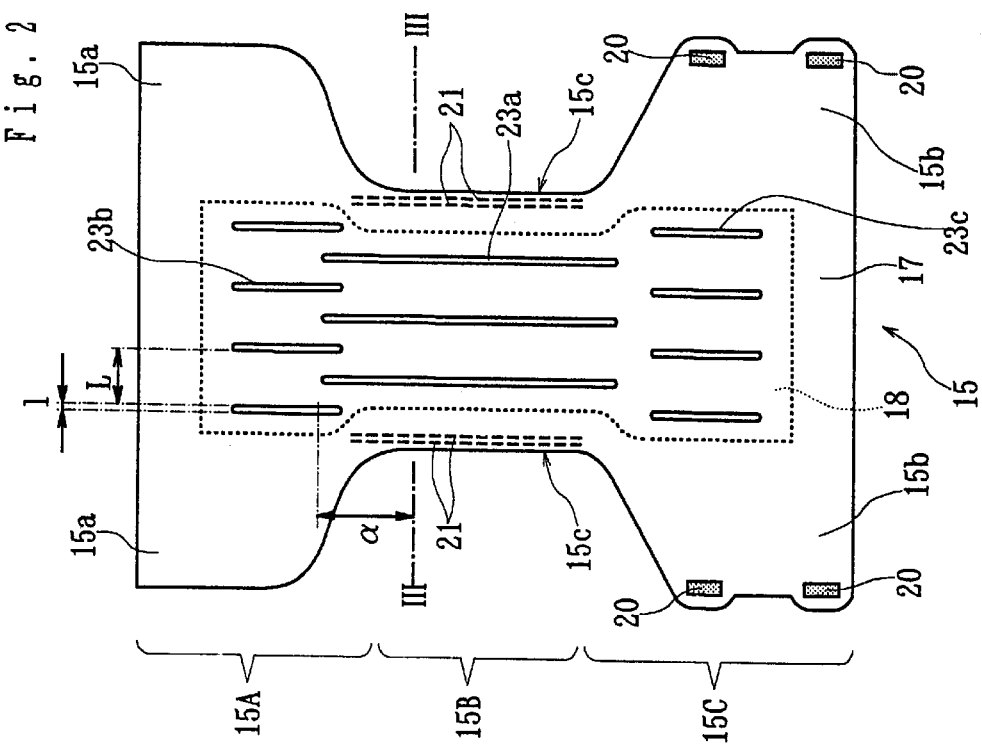
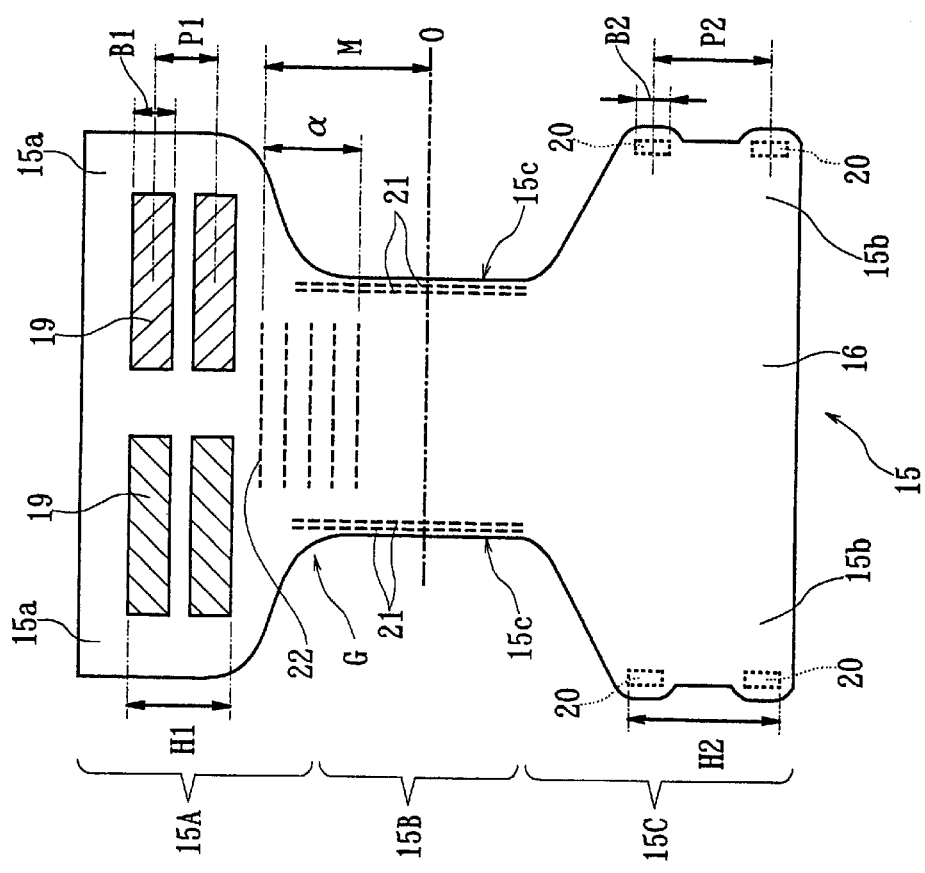
Fig. 2 (A)
Fig. 2 (B)

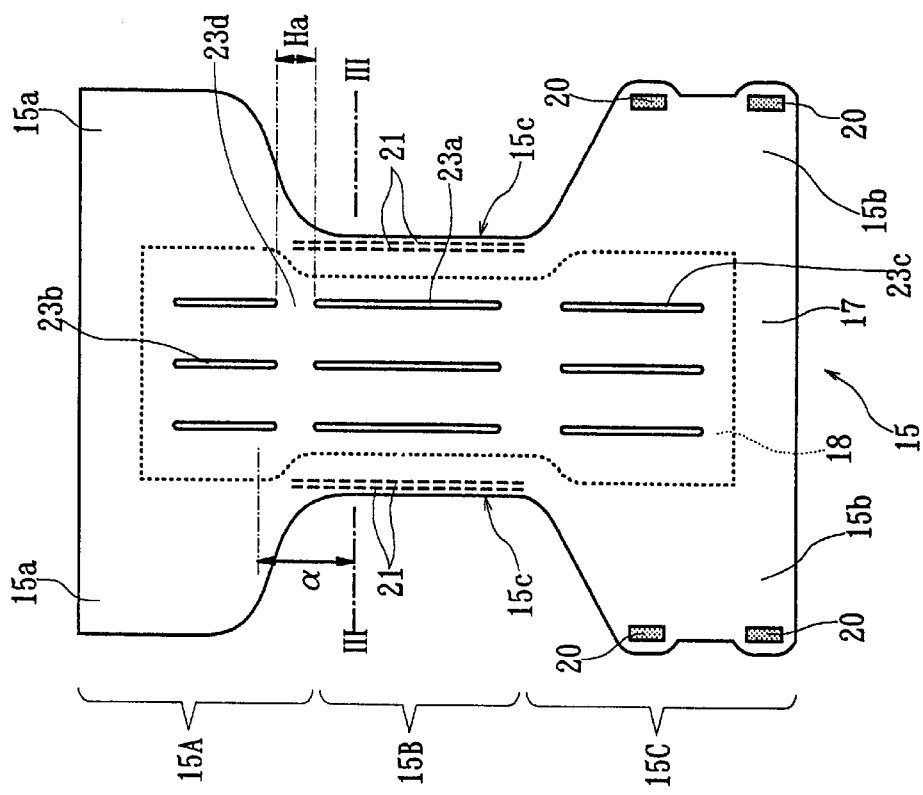
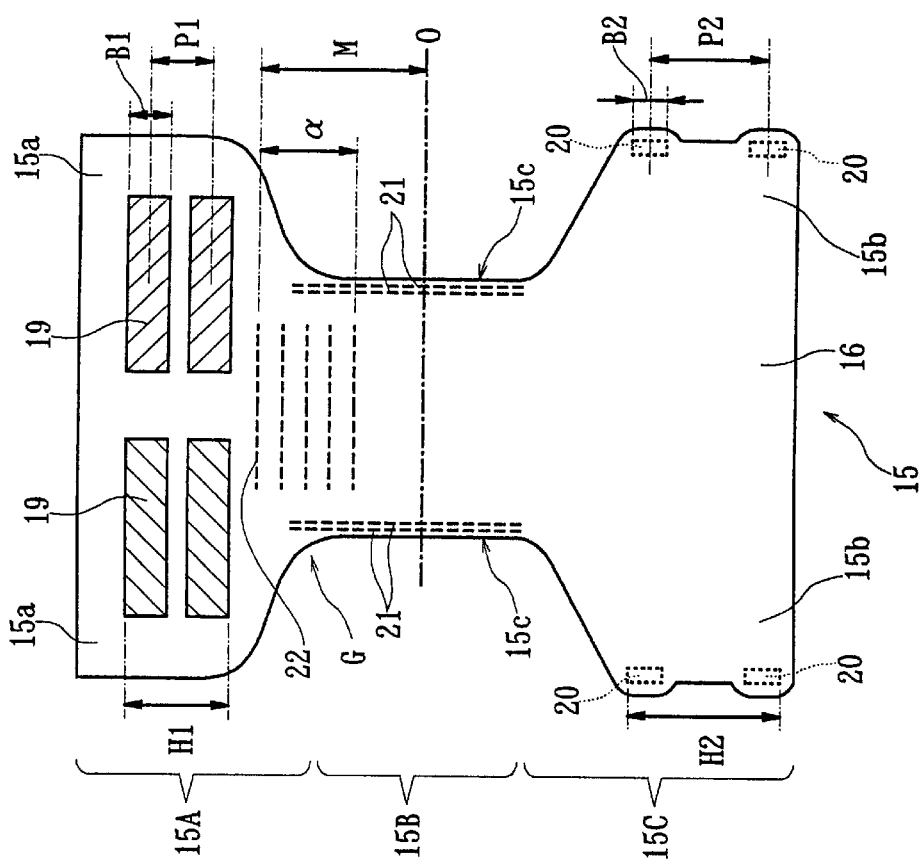

DISPOSABLE DIAPER

BACKGROUND OF THE INVENTION

1. Field of the Invention

The present invention relates to a disposable diaper which fits the body of a wearer, more particularly to a disposable diaper which can prevent the positional shift of a protector against incontinence and the side leaking of urine when the protector is used.

2. Prior Art

A disposable diaper comprises a back sheet, a top sheet and an absorbent core interposed between the back and top sheets. The back sheet is made of a liquid non-permeable but finely air permeable resin sheet so as to prevent the outside oozing of urine. Furthermore, the top sheet to face the skin of a wearer is made of a material gentle to the skin, such as non-woven fabric or soft porous sheet, both liquid permeable, so that fluids such as urine permeates through the top sheet into the absorbent core. As the absorbent core, additionally, use is made of crushed pulp or a mixture of crushed pulp and super absorbent polymer.

In order to fit the body outline of a wearer, the absorbent core is produced by cutting into a sandglass-like form. After cutting, the absorbent core is interposed between the back sheet and the top sheet. The back sheet and the top sheet both are of a shape similar to the shape of the absorbent core but with a larger outline than the absorbent core. At both ends thereof where no absorbent core is present, these back sheet and top sheet are bonded together by means of a hot-melt adhesive.

A back waist region of disposable diaper is attached to the dorsal area of a wearer; a crotch region thereof is attached to the crotch thereof; and a front waist region thereof is attached to the abdominal area thereof. By drawing forward flaps of the back waist region which flaps elongate in the width direction of the diaper to overlay the flaps over the front waist region, the front waist region and the flaps are fastened together. Thus, the diaper is completely worn.

Generally, flat elastic braids capable of elongating toward the longitudinal direction (lengthwise direction) of the diaper are partially bonded, at their elongated state between the back sheet and the top sheet, to both sides of the crotch region in the crosswise direction (width direction) by means of a hot-melt adhesive, thereby forming gatherings to be applied to the thigh parts of a wearer.

A disposable diaper for adults is far larger than a disposable diaper for infants and toddlers, requiring a larger volume of raw materials for one diaper piece and thus costing high per unit price. Therefore, it is not economical to change the diaper for adults to new one in each time of excretion of urine. Accordingly, a protector against incontinence is generally used in combination with the diaper. After urine excretion, then, only the protector against incontinence is changed.

Such a protector against incontinence is formed of a lamination body in a sheet-like form, comprising an outer sheet comprising for example a liquid non-permeable resin sheet, an inner sheet comprising for example a non-woven fabric, and an absorbent core interposed between the outer and inner sheets. At ends in the lamination body in the width direction and the longitudinal direction where no absorbent core is present, the outer sheet and the inner sheet are bonded together by means of a hot-melt adhesive. To the ends in the width direction, additionally, elastic members such as flat elastic braids are partially bonded at its elongated state between the outer sheet and the inner sheet. The elastic member forms a gathering.

The lamination body in the sheet-like form is preliminarily deformed in the shape of a cone so that the center of the lamination body in the longitudinal direction forms the peak of the cone when the protector against incontinence is worn. Through an adhesive part provided to the lamination body, both ends of the lamination body are bonded together.

The disposable diaper should be used in such a manner that when a male wearer wears the protector against incontinence, the protector adheres to the top sheet of the diaper in the crotch region thereof by another adhesive part provided to the protector to prevent the shift of the protector in the diaper.

The same protector may be used for females. In this case, the protector is applied to the diaper such that, while the longitudinal direction of the lamination body should be aligned along the longitudinal direction of the diaper, the outer sheet of the protector should face the top sheet of the diaper to overlay the protector over the crotch region of the diaper. Then, the adhesive part of the protector adheres to the top sheet of the diaper to prevent the shift of the protector on the diaper. In such manner, the protector is used.

As described above, the diaper is in a sandglass-like form, wherein the width of the crotch region is narrower than the widths of the front waist region and the back waist region. Because urine is mainly absorbed in the crotch region, however, the crotch region should be wide enough to absorb urine. Therefore, the crotch region is generally formed at a larger width than the width of the crotch of a wearer.

Therefore, in the case when such a diaper is worn, the crotch region expands in a bag-like shape because the crotch region is pressed by the thigh parts of a wearer from both sides in the width direction, so that a space is formed between the crotch of the wearer and the diaper. When the diaper is used in combination with a protector against incontinence, therefore, the protector is positioned in the front side of the expanded crotch region of the diaper. Then, the protector is not pressed sufficiently against the body. When the wearer makes a motion, therefore, the protector so readily makes a positional shift in the diaper that the protector cannot effectively absorb urine.

In a border region between the front waist region and the crotch region of the diaper, in particular, the individual dimensions of these regions in the width direction are prominently different from each other. When the crotch region is pressed by the thigh parts of a wearer, therefore, the border region is apt to expand more on the side closer to the front waist region, and the protector for males is mounted on this side of the border region. When the front waist region side of the border region expands as has been described above, therefore, the force of the diaper to press the protector is weakened especially for males, to readily cause the positional sift of the protector.

Furthermore, when the diaper is directly worn without any protector against incontinence, excretion such as urine and feces readily leaks from the front waist region side of the border region.

When the direction from the front waist region through the crotch region to the back waist region is defined as the longitudinal direction of the diaper, conventionally, the pitch of the front retaining fasteners arranged on the front waist region in the longitudinal direction has been almost the same as the pitch of the back retaining fasteners arranged on the flaps of the back waist region in the longitudinal direction. When the flaps of the back waist region are overlaid over the surface of the front waist region to fasten the front and back retaining fasteners together, therefore, the diaper forms a cylindrical shape at a portion to be applied to the wearer's hips and waist. The dimension of the inner diameter (diameter size) of the cylinder is kept at almost the same value all through the longitudinal direction of the cylinder.

However, the outer size of the waist (waist size) of humans is generally smaller than the outer size of the hips (hip size) thereof. Therefore, in the diaper with the front and back retaining fasteners fastened together, the inner size of the cylinder is adjusted to the outer size of the hips, so that some space is formed between the diaper and the wearer's waist. When the front and back retaining fasteners are fastened together, therefore, the diaper cannot fit the waist, causing insufficient fastening of the diaper around the waist, which possibly causes certain positional shift of the diaper. Compared with infants and toddlers, adult body shape has such a larger difference in outer size between the hips and the waist that the diaper can hardly be fastened sufficiently around the waist.

Even in the diaper for new born babies or infants, furthermore, since the absorption core in the crotch region is more voluminous, the expansion of the diaper in the crotch region is increased when the diaper is worn. If the diaper has a cylindrical shape with a uniform inner size, therefore, it is very difficult to fasten sufficiently the diaper around the waist of the wearer or the abdomen thereof.

It is an object of the present invention to provide a disposable diaper wherein a border region between a front waist region and a crotch region is prevented from expanding toward the direction free from the body of a wearer.

It is another object of the present invention to provide a disposable diaper which is securely fastened around the waist of a wearer.

SUMMARY OF THE INVENTION

The present invention provides a well-fitting disposable diaper having a front waist region to be applied to the abdominal area of a wearer, a crotch region to be applied to the crotch thereof and a back waist region to be applied to the dorsal area thereof, arranged in a longitudinal direction of the diaper in this order, comprising, a liquid non-permeable back sheet, a liquid permeable top sheet, an absorbentcore interposed between the back sheet and the top sheet and extended from the front waist region, the crotch region to the back waist region, first and second thin parts where no absorbent core is present or where the thickness of the absorbent core is reduced being formed separately in a linearly elongating fashion in the longitudinal direction, the first thin parts having intervals therebetween in a width direction perpendicular to the longitudinal direction being elongated from the crotch region toward the front waist region and the back waist region, the second thin parts having intervals therebetween in the width direction being elongated from the front waist region toward the crotch region, and a plurality of elastic members elongating in the width direction, the elastic members being arranged on a region, which is positioned on the side of the front waist region from the center of the crotch region and includes a border between the front waist region and the crotch region, one end portions of the first thin parts toward the front waist region and one end portions of the second thin parts toward the crotch region, thereby forming a front gathering.

The present invention further provides a well-fitting disposable diaper having a front waist region to be applied to the abdominal area of a wearer, a crotch region to be applied to the crotch thereof and a back waist region to be applied to the dorsal area thereof, arranged in a longitudinal direction of the diaper in this order, comprising, a liquid non-permeable back sheet, a liquid permeable top sheet, an absorbent core interposed between the back sheet and the top sheet, and a first retaining means and a second retaining means to be attached to each other when the diaper is applied to a wearer, the first retaining means being disposed on the back sheet in the front waist region, the second retaining means being composed of two pairs of back retaining members disposed on both sides of the top sheet in the back waist region in a width direction perpendicular to the longitudinal direction, the back retaining members in each pair having an interval therebetween in the longitudinal direction, a total dimension of the back retaining members in each pair and the interval therebetween in the longitudinal direction being larger than a dimension of the first retaining means in the longitudinal direction.

BRIEF DESCRIPTION OF THE DRAWINGS

FIGS. 2(A) and 2(B) are developed plane views of the diaper of the present invention; FIG. 2(A) is a developed plane view of the front side of the diaper; and FIG. 2(B) is a developed plane view of the back side thereof;

FIG. 3(A) depicts the diaper at a flat state without shrinkage; FIG. 3(B) depicts the diaper at a state when elastic members shrink to form a front gathering G;

FIGS. 4(A) and 4(B) are developed plane views of another example of the diaper of the present invention; FIG. 4(A) is a developed plane view of the front side of the diaper; and FIG. 4(B) is a developed plane view of the back side of the diaper;

FIG. 6(A) is a developed view; and FIG. 6(B) is a perspective view of the protector at a state when it is used.

DETAILED DESCRIPTION OF THE PREFERRED EMBODIMENTS

Figure 1:
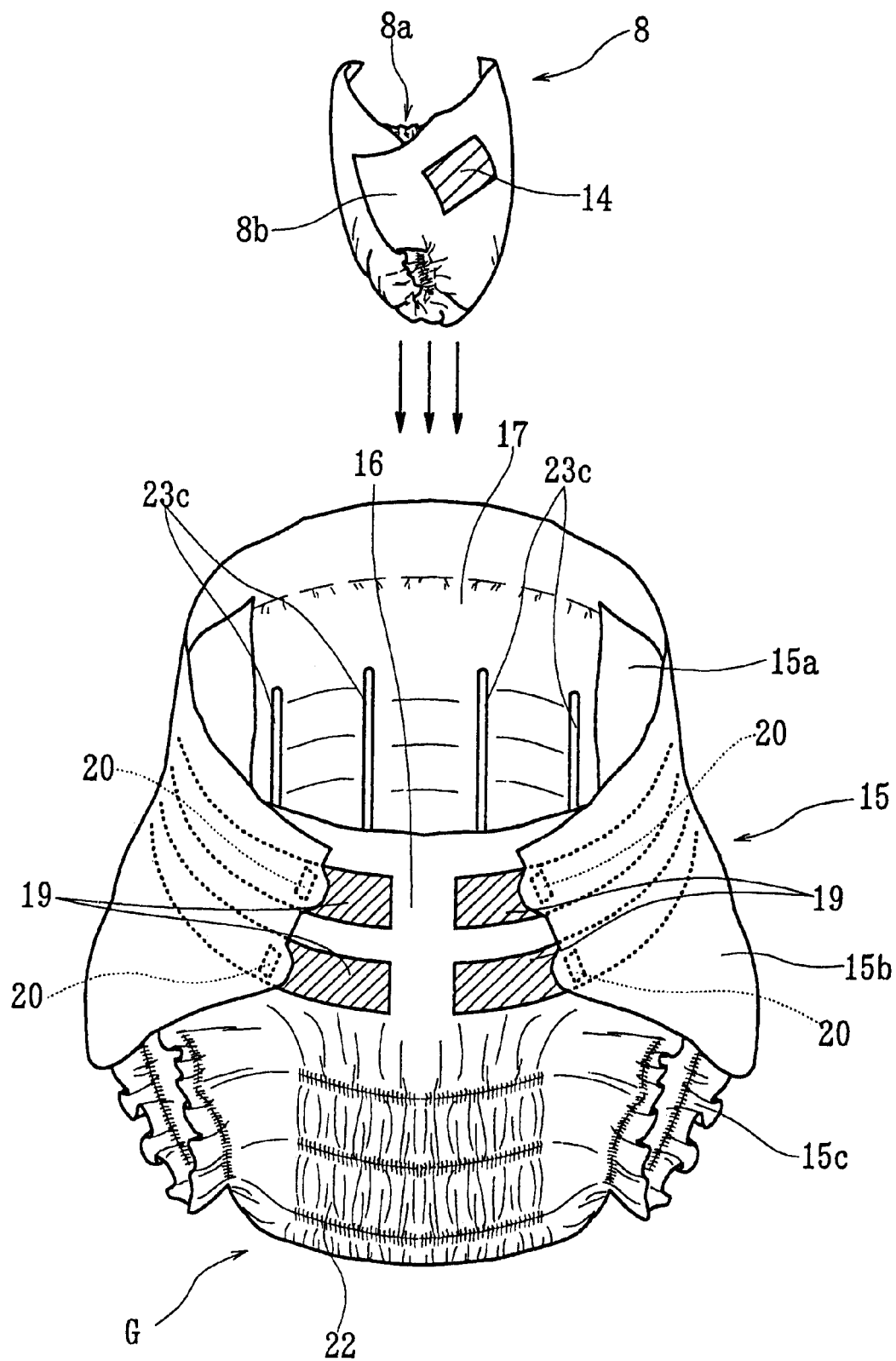
FIG. 1 is a perspective view of the diaper of the present invention at a state when the diaper is worn.

The present invention will be described in the following embodiments with reference to the drawings hereinbelow.

A diaper 15 is formed of a lamination body, comprising a back sheet 16 and a top sheet 17, and an absorbent core 18 interposed between the back and top sheets. The back sheet is made of a liquid non-permeable but air permeable resin sheet, so as to prevent the oozing of urine outside. The top sheet 17 is made of a liquid permeable non-woven fabric, for example, with a basis weight of 15 g/m$^2$ or more to 25 g/m$^2$ or less.

As the absorbent core 18, use is made of crushed pulp or a mixture of crushed pulp with super absorbent polymer, capable of well absorbing urine but never causing any unpleasant feeling for the wearer. As the crushed pulp for use as the absorbent core 18, generally, use is made of light weight crushed pulp with for example a specific gravity of 100 g/m² or more to 500 g/m² or less. The absorbent core 18 is produced by preparing crushed pulp or super absorbent polymer in a sheet-like form, thereafter preparing the thickness thereof uniformly and cutting the resulting sheet in a sandglass-like form with the width of a crotch region 15B narrower. The region surrounded by dotted line in FIG. 2(B) is a region where the absorbentcore 18 is placed.

As shown in FIGS. 2(A) and 2(B), front flaps 15*a*, 15*a* protruding in the crosswise direction of the diaper are formed in a front waist region 15A of the diaper 15. In a back waist region 15C, back flaps 15*b*, 15*b* are formed, which are present on both sides of the diaper in the crosswise direction and protrude in the crosswise direction of the back waist region 15C.

The front flaps 15*a*, 15*a* and the back flaps 15*b*, 15*b* are formed by protruding the back sheet 16 and the top sheet 17 in the crosswise direction of the diaper and bonding the back and top sheets 16 and 17 together by means of a hot-melt adhesive 24, with no absorbent core 18 interposed between the back sheet 16 and the top sheet 17. Alternatively, a resin sheet or a non-woven fabric with a larger base weight, which is newly cut in a given shape, may be mounted on the back sheet 16 and the top sheet 17 to form the front flaps 15*a*, 15*a* and the back flaps 15*b*, 15*b*.

On the surface of the back sheet 16 are fixed two pairs of front retaining members 19 as a first retaining means, the front retaining members 19, 19 in each pair having an interval along the longitudinal direction, in the front waist region 15A. Additionally, two pairs of back retaining members 20 as a second retaining means are arranged, the back retaining members 20, 20 in each pair having an interval along the longitudinal direction, on top parts of the back flap 15*b* (both sides of the back waist region 15C). When the diaper 15 is worn, the back waist region 15C is applied to the dorsal area of a wearer while the crotch region 15B is applied to the crotch thereof and the front waist region is applied to the abdominal area thereof. Then, the back flaps 15*b*, 15*b* are overlaid on the back sheet 16 in the front waist region 15A to fasten the back retaining members 20 with the front retaining members 19.

As shown in FIG. 2(A), the aligning pitch P2 between the center lines of the pair of back retaining members 20 aligned in the longitudinal direction is larger than the aligning pitch P1 between the center lines of the pair of front retaining members 19 aligned in the longitudinal direction. The total dimension H2 of the pair of back retaining members 20, 20 and the interval therebetween in the longitudinal direction is larger than the total dimension H1 of the pair of front retaining members 19, 19 and the interval therebetween in the longitudinal direction. Furthermore, the width dimension B1 of the front retaining members 19 in the longitudinal direction is sufficiently larger than the width dimension B2 of the back retaining members 20 in the longitudinal direction.

In the diaper for adults (aged people), for example, the aligning pitch P1 of the front retaining members 19 is 80 mm, while the aligning pitch P2 of the back retaining members 20 is 135 mm. The ratio of P2/P1 is almost 3.1/1.9, preferably 3/2 or more. The total dimension H1 is 130 mm while H2 is 165 mm, and the difference therebetween is 35 mm. Furthermore, the width dimension B1 is 50 mm, while the width dimension B2 is 30 mm, and the ratio of B1/B2 is preferably 5/3 or more. Furthermore, the front retaining members 19 are of a rectangular shape or a band-like shape, with the longer side toward the crosswise direction of the diaper, and the longer side thereof is for example 235 mm.

Because the dimension of the front retaining members 19 is large in the crosswise direction, the positional relation between these retaining members 19 and 20 can make a certain shift for wearing, depending on the waist size of a wearer. Additionally, the aligning pitch P2 of the back retaining members 20 is larger than the aligning pitch P1 of the front retaining members 19, while the total dimension H2 of the pair of back retaining members 20 and the interval therebetween in the longitudinal direction is larger than the total dimension H1 of the pair of front retaining members 19 and the interval therebetween in the longitudinal direction. When the diaper is worn, therefore, the side edges of the back flaps 15*b* are obliquely applied to the front waist region 15A, as shown in FIG. 1, while the sides of the back retaining members 20, 20 face obliquely to the sides of the front retaining members 19.

As shown in FIG. 1, accordingly, the position where the front retaining members 19 positioned upward are attached with the back retaining members 20 is present more inward (closer to the front center line of the worn diaper) than the position where the front retaining members 19 positioned downward are attached with the back retaining members 20. At such state, the back retaining members 20 can be fastened nearly to the center of the front retaining members 19 in the longitudinal direction. Accordingly, when the diaper is worn by a wearer, the diaper is narrowed upwardly, so that the diaper is easy to fit the body of a wearer and can securely fasten the body around the waist.

Incidentally, in the present invention, the pair of front retaining members 19, 19, which are aligned in the longitudinal direction and have the total dimension H1, may satisfactorily be replaced with a single retaining member having a large dimension in the longitudinal direction. That is, the first retaining means may be formed by arranging two retaining members on the right and left sides of the front waist region 15A, respectively. In any case, it is a requirement that the dimension H1 of the region, which is capable of fastening and formed by the first retaining means, is smaller than the dimension H2.

In the embodiment, furthermore, the back retaining members 20 are retaining sheets made of resin, where a great number of retaining protrusions of a mushroom shape or a hook shape having a retaining head on the top are formed. On the other hand, the front retaining members 19 are woven, tricot-knitted fabrics made of polyester fibers, or non-woven fabrics. Alternatively, as the back retaining members 20, an adhesive tape may be arranged satisfactorily instead of the retaining sheet, while instead of a woven or non-woven fabric, a film may satisfactorily be arranged as the front retaining members 19. In this case, the adhesive tapes (back retaining members 20) adhere to the surface of the film (front retaining members 19) when the diaper is worn.

On both edge parts of the crotch region 15B of the diaper 15, for example, two flat elastic braids 21, 21 at their elongated state in the longitudinal direction and at an interposed state between the back sheet 16 and the top sheet 17 are bonded to the back and top sheets. The crotch region 15B shrinks in the longitudinal direction via the flat elastic braids 21, 21 to form crinkles to prepare thigh part gatherings 15*c*. Through the thigh part gatherings 15*c*, the diaper turns into a solid shape with the back sheet 16 protruding.

When the diaper 15 is worn, the thigh part gathering 15c appropriately fastens the leg groin of a wearer to prevent the forming of a space between the thigh part and the diaper, so that the diaper can fit the thigh part of the wearer.

Figure 3:
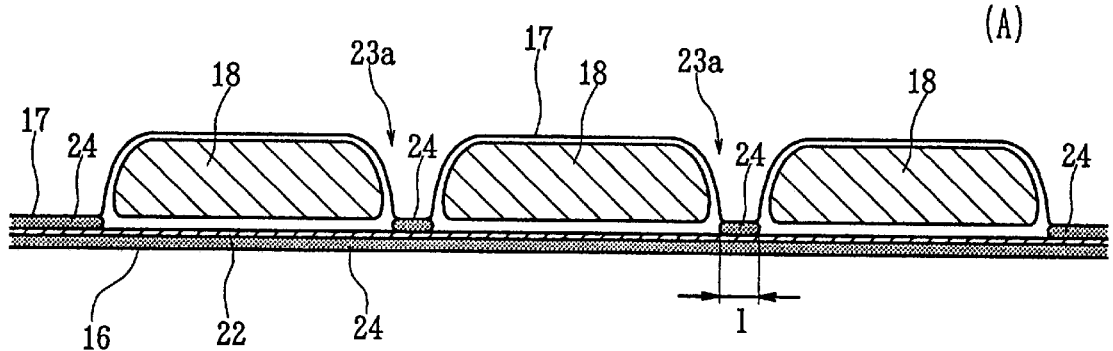
FIGS. 3(A) and 3(B) are cross sectional views of FIG. 2 or FIG. 4 along line III—III.
Figure 3:
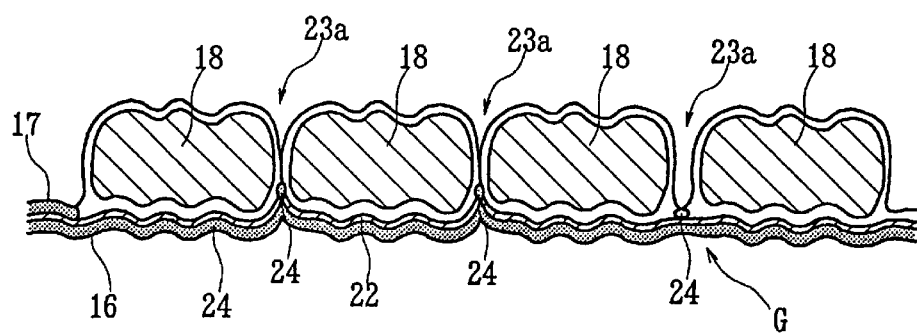

As shown in FIG. 2(A), at a part closer to the side of the front waist region from the center part of the crotch region 15B of the diaper 15 in the longitudinal direction, more specifically in a region α over the crotch region 15B and the border region between the crotch region 15B and the front waist region 15A, a plurality of elastic members 22 such as flat elastic braid elongating in the crosswise direction of the diaper are arranged at intervals. As shown in FIG. 3(A), the elastic members 22 are arranged between the absorbent core 18 and the back sheet 16. Then, the elastic members 22 are bonded and fixed on the back sheet 16 by means of a hot-melt adhesive 24 while the elastic members are at an elongated state to have 1.5 to 3-fold length, preferably 2 to 2.5-fold length to the initial length. The elastic members 22 and the back sheet 16 are bonded together over the whole length of the elastic members 22 by means of the hot-melt adhesive 24. Otherwise, the elastic members 22 and the back sheet 16 are partially bonded together by means of the hot-melt adhesive 24. As shown in FIG. 3(A), furthermore, the elastic members 22, the top sheet 17 and the back sheet 16 are bonded together and fixed by means of the adhesive 24 in thin parts 23a.

Figure 6:
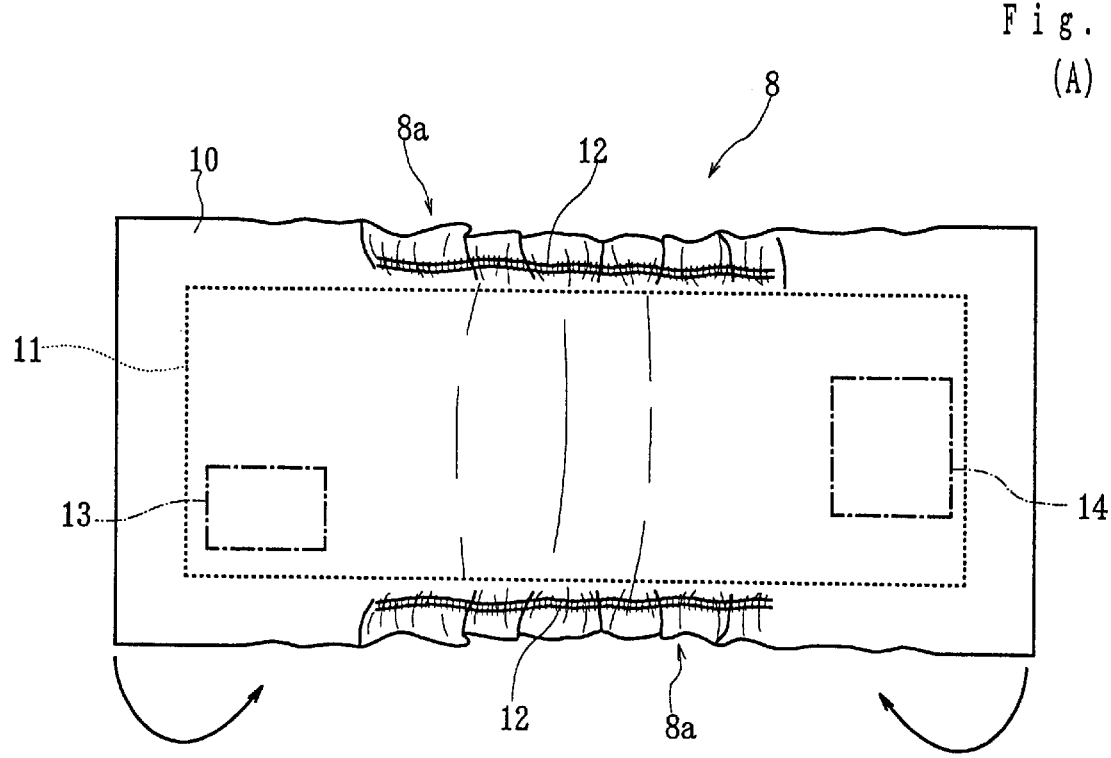
FIG. 6 depicts a protector against incontinence.
Figure 6:
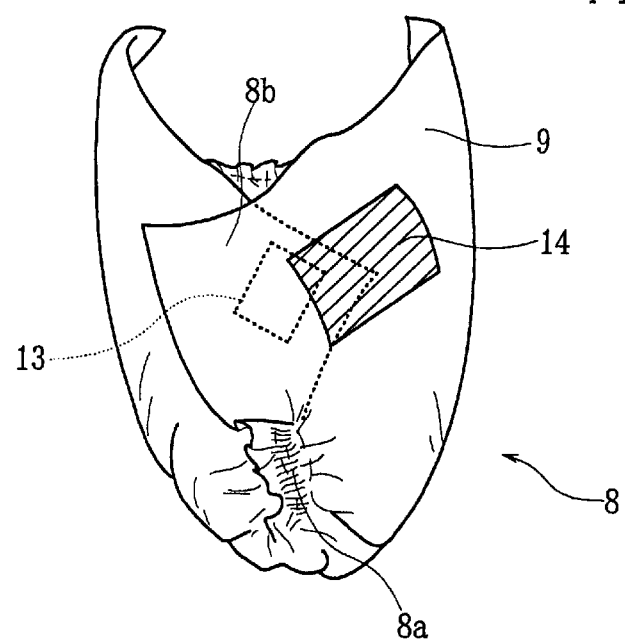

The diaper shrinks in the region α in the crosswise direction through the elastic members 22 to form a front gathering G. In one example shown in FIG. 2(A), the front gathering G is formed in the crotch region 15B, and the border region between the crotch region 15B and the front waist region 15A. When the diaper is used in combination with a protector against incontinence 8 for males as shown in FIGS. 6(A) and 6(B), the region α where the elastic members 22 are arranged nearly corresponds to the region where the protector against incontinence 8 is to be mounted. In this case, the distance from the center line O of the crotch region 15B in the crosswise direction to the elastic member 22 arranged at the far end toward the front waist region 15A (shown as M in FIG. 2(A)) is preferably about 250 mm.

As shown in FIG. 2(B), a plurality of thin parts 23a, 23b and 23c are formed on the region where the absorbent core 18 is presented on the diaper 15. The term "thin part" herein used means a part where no absorbent core is present in a linearly elongating fashion and the top sheet and the back sheet is bonded together or a part where the thickness of the absorbent core is reduced in a linearly elongating fashion. The thin parts 23a are arranged as three lines elongating linearly in the longitudinal direction in the crotch region 15B and having given intervals in the crosswise direction therebetween. Additionally, the thin parts 23b and 23c are arranged as four lines elongating linearly in the longitudinal direction and having given intervals in the crosswise direction therebetween. The thin parts 23a arranged in the crotch region 15B, and the thin parts 23b and 23c arranged in the front waist region 15A and the back waist region 15C, are independently formed and separated from each other.

At corresponding end portions, the thin parts 23a arranged in three lines in the crotch region 15B, and the thin parts 23b arranged in four lines in the front waist region 15A, are alternately arranged in the border region between the crotch region 15B and the front waist region 15A. The end portions of the thin parts 23a and 23b arranged alternately are positioned in the region α where the elastic members 22 are arranged to form the front gathering G. It is not required that the end portions of the thin parts 23a and 23b accurately correspond to the border between the crotch region 15B and the front waist region 15A and the end portions may reside at a part closer to the side of the crotch region 15B in the border region or at a part closer to the side of the front waist region 15A in the border region. The end portions preferably reside in the region α. However, the end portions may be more or less outside the region α only if the shrinkage force from the elastic members 22 is given to the end portions.

In the embodiment of the present invention as shown in FIGS. 3(A) and 3(B), no absorbent core 18 is present in the thin parts 23a, 23b or 23c. At the thin parts 23a, 23b and 23c, the back sheet 16 and the top sheet 17 are directly bonded together by means of the hot-melt adhesive 24 or the like. At the thin parts 23a, 23b and 23c where the elastic members 22 are interposed, preferably, the top sheet 17 and the back sheet 16 are bonded to the elastic members 22.

The thin parts 23a, 23b and 23c elongating linearly in the longitudinal direction are formed on the diaper 15, and in the region α where one end portions of the thin parts 23a and 23b are located, elastic shrinkage force from the elastic members 22 is given to the direction vertical to the thin parts.

When the elastic shrinkage force is larger than the rigidity of the absorbent core 18, thick parts in the absorbent core excluding the thin parts are drawn from both the sides in the crosswise direction of the diaper as shown in FIG. 3(B), so that the adjacent thick parts having the thin part 23a therebetween adhere to each other. Thereafter, the thick parts excluding the thin parts shrink more in the crosswise direction, where the absorbent core 18 deforms to protrude toward the inside of the diaper (the body side of a wearer). Thus, the region α of the diaper 15 adheres to the body of a wearer, with no forming of any space between the diaper 15 and the body of a wearer. In order to deform the diaper 15 as has been described above, two or more elastic members may satisfactorily be arranged, each elastic member having an elastic force of 10 g or more when the elastic member is elongated 2-fold to the initial length, provided that the rigidity of the absorbent core 18 as measured according to JIS P8125 is 3 g·cm or more to 20 g·cm. Then, the elastic shrinkage force from the elastic members 22 exceeds the rigidity of the absorbent core 18, so that the thick parts excluding the thin parts can shrink. If the elastic shrinkage force of the elastic members 22 is too strong, however, the width dimension of the diaper 15 becomes too small. The upper limit of the elastic force per one elastic member 22 is about 100 g, while the number of the elastic members 22 varies depending on the elastic force from one elastic member. Generally, however, the number of the elastic members is preferably about 2 to 50.

When the elastic members, the back sheet and the top sheet are bonded together at the thin parts, in particular, the shrinkage force from the elastic members directly acts on the top sheet and the back sheet. Then, the thick parts are readily drawn together.

In the diaper shown in FIG. 2(B), furthermore, because the end portions of the thin parts 23a and the end portions of the thin parts 23b are alternately arranged and overlapped in the crosswise direction in the region α under the influence of the elastic force from the elastic members 22, the number of the thick parts divided by the thin parts 23a and 23b is increased in the border region between the crotch region 15B and the front waist region 15A. Therefore, at the border region, the diaper readily shrinks in the crosswise direction, so that the diaper hardly expands forward.

Therefore, the diaper 15 fits the body with no forming of any space between the border region of the diaper 15 and the body of a wearer, to prevent the leaking of urine and feces. When the diaper is directly worn, furthermore, urine is never concentrated at one spot because of the presence of the thin parts 23a of the crotch region 15B, so that urine is readily dispersed over the absorbent core in the front waist region 15A and the back waist region 15B.

The thin parts 23a of the crotch region 15B and the thin parts 23b of the front waist region 15A, both receiving the shrinkage force from the elastic members 22, are formed in such a manner that the adjacent thin parts generally have an interval (length L in FIG. 2(B)) of about 10 mm or more to 100 mm or less and the width of the thin part 23a or 23b (length l in FIG. 2(B)) is 1 mm or more to 15 mm or less. Within the range of such numerical figures, the thin parts 23a and 23b are to be formed. In such case, the diaper 15 readily deforms along the body outline of a wearer, and urine is readily dispersed.

When a male adult wears the diaper 15, the protector against incontinence 8 shown in FIGS. 6(A) and 6(B) is generally worn.

The protector against incontinence 8 is formed of a lamination body in a sheet-like form, comprising an outer sheet 9 such as a liquid non-permeable resin sheet, an inner sheet 10 such as a non-woven fabric and an absorbent core 11 interposed between the inner and outer sheets. At ends of the lamination body in the longitudinal direction and the width direction, where no absorbent core is present, the outer sheet and the inner sheet are bonded together by means of a hot-melt adhesive. At the ends in the width direction, elastic members 12 such as flat elastic braids elongating in the longitudinal direction are interposed and partially bonded at its elongated state between the outer sheet and the inner sheet. The elastic members form gatherings 8a.

The protector against incontinence 8 is formed into a bag-like shape for males as shown in FIG. 6(B), by deforming the sheet-like lamination body shown in FIG. 6(A) in a conical shape while the outer sheet 9 faces outward. Then, the protector is worn such that the overlaying part 8b is not applied to the abdominal area of the body. While the protector against incontinence 8 is worn, the back waist region 15C of the diaper 15 is applied to the dorsal area; the crotch region 15B is applied to the crotch and the front waist region 15A is applied to the abdominal area. By adhesion bonding an adhesive part 14 disposed on the protector against incontinence 8 to the top sheet 17 of the front waist region and then fastening the front and back retaining members 19 and 20 together, the diaper 15 is worn. Then, the diaper 15 deforms through the thin parts 23a, 23b and 23c along the body outline of the body of the wearer, and furthermore, the region α in the border between the front waist region 15A and the crotch region 15B deforms along the shape of the protector against incontinence 8. Subsequently, the front gathering G as applied to the crotch of the wearer elongates along the outer shape of the protector against incontinence 8, to elastically fit the protector against incontinence 8, whereby the protector against incontinence 8 can be pressed so that the protector might never be free from the body of the wearer. Thus, the protector against incontinence 8 does not make any shift in position, so that the protector against incontinence 8 effectively absorbs urine.

When the diaper 15 is used for females, additionally, the protector against incontinence 8 is overlaid on the top sheet 17 of the crotch region 15B of the diaper 15 while the protector against incontinence 8 remains as the sheet-like form as shown in FIG. 6(A), and at such state, the diaper 15 is worn. The front gathering G is in contact to the protector against incontinence 8, so that the protector against incontinence 8 can be retained at a stable state by means of the front gathering G. When the protector against incontinence 8 is used for females, preferably, elastic members 22 are arranged more closely to the side of the center line O shown in FIG. 2(A).

When the protector against incontinence 8 is used in such manner, the diaper thus worn expands at the crotch and the hips of the wearer. As has been described above, however, the diaper thus expanded can be securely fastened around the waist of the wearer due to the front and back retaining members 19, 20.

When the diaper 15 is singly worn with no use of any protector against incontinence, the front gathering G deforms along the shape of the crotch of a wearer to elastically fit the crotch. Thus, no space is formed between the body of the wearer and the diaper 15, so that the side leaking of urine and feces from the diaper can be prevented, whereby urine and feces can be retained securely in the diaper 15. Through the thin parts 23a, 23b and 23c, urine can be dispersed not only over the crotch region, without any concentration, so that the absorption potency of the diaper 15 can be improved.

As shown in FIGS. 2(A) and 2(B), furthermore, the thin parts 23b formed in the front waist region 15A elongate to a position where the thin parts 23b are overlaid over the front retaining members 19. When the back flaps 15b, 15b are overlaid on the front waist region 15A to fasten the front and back retaining members 19, 20 together, the surface of the front waist region 15A readily deforms. If the front gathering G is formed around the front retaining members 19 as shown in FIG. 2(A), in particular, the shrinkage force of the elastic members 22 acts on the front retaining members 19 so that the front retaining members 19 readily receive the shrinkage force in the crosswise direction.

At] the front retaining members 19, the width of the thin part 23b is narrowed similarly as shown in FIG. 3(A), because of the shrinkage force, but the thick part where the absorbent core is present between the thin parts 23b is still flat. At the front retaining members 19, therefore, the thick part is at a flat state and the flat area of the thick part is relatively large. Hence, the back retaining members 20 can be bonded to the flat area of the front retaining members 19. Thus, the retaining strength between the front and back retaining members 19, 20 can be kept large.

FIGS. 4(A) and 4(B) are developed plane views of another example of the diaper of the present invention. As shown in FIG. 4(B), the end portions of the thin parts 23a in the crotch region 15B and of the thin parts 23b in the front waist region 15A are separated from each other in the longitudinal direction, and the region of a given width Ha between the thin parts 23a and 23b in the longitudinal direction forms a thick part 23d with no thin part formed thereon. The thick part 23d is positioned in the region α where the elastic members 22 are arranged to form the front gathering G.

As shown in FIG. 3(B), after the shrinkage of the elastic members 22 in the crosswise direction, deep recesses are formed at the thin parts 23a or 23b, to make the irregularity of the top sheet 17 more prominent. When the thick part 23d is formed, however, the irregularity of the top sheet 17 is slightly reduced at the thick part 23d, to consequently enlarge the relatively flat area. When the protector against incontinence 8 is positioned inside the front gathering G and the adhesive part 14 adheres to the thick part 23d, the touch area between the adhesive part 14 and the top sheet 17 can be enlarged because no thin part is present. Thus, the adhesion strength of the protector against incontinence 8 to the diaper can be enhanced, whereby the shift of the protector against incontinence 8 can be prevented.

The thick part 23d is formed at a position to be spotted with urine. Because a greater volume of the absorbent core 18 is present at the thick part 23d, the reduction of the absorbed urine in volume can be prevented.

Figure 5:
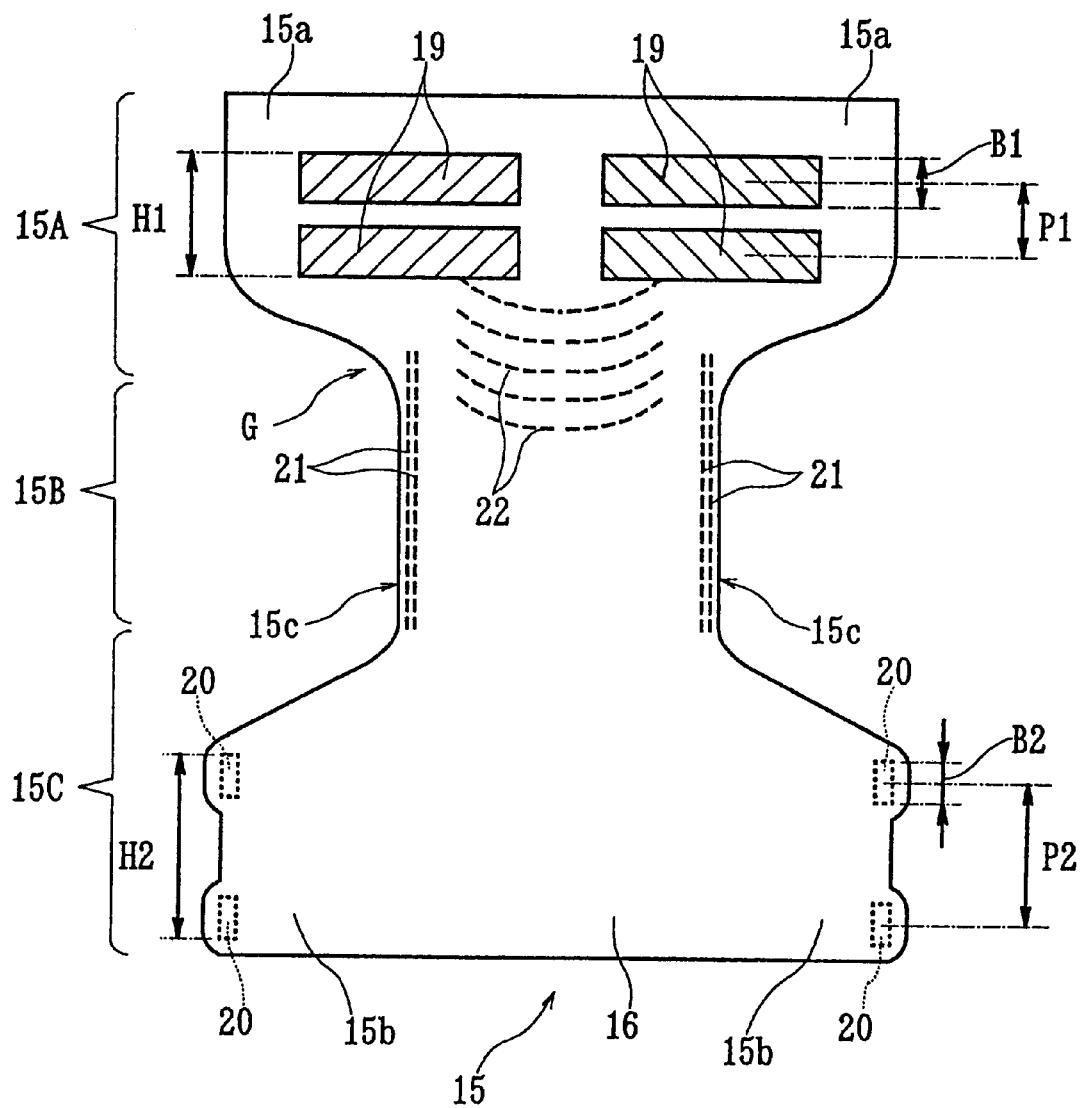
FIG. 5 is a developed view of the other example of the diaper of the present invention.

FIG. 5 depicts still another embodiment of the diaper of the present invention, which is a view of the diaper 15 at a developed state, as viewed from the outside. In the embodiment, the elastic members 22 are arranged in such a curved fashion to protrude at the center thereof in the crosswise direction toward the center of the crotch region 15B of the diaper 15. If the elastic members 22a are arranged in such fashion, the diaper 15 deforms more fittingly along the protector against incontinence 8 and the crotch shape of a wearer, so that the diaper 15 can fit the body more.

The present invention has been described for an open type diaper, but the effect of arranging the thin parts 23a, 23b and 23c and the effect of forming the front gathering G, in accordance with the present invention, are also exerted even if the thin parts are formed in a brief-type diaper. Such thin parts may satisfactorily be formed in diapers not only for adults but also for infants (and toddlers).

As has been described in detail insofar, in the diaper of the present invention, the elastic members are arranged in the front waist region or the border region between the crotch region and the front waist region to form the front gathering. In the region where the front gathering is formed, the crotch of a wearer can be pressed elastically. Thus, no space is formed between the diaper and the crotch of a wearer, so that the diaper can fit the crotch.

Because the thin parts elongating in the longitudinal direction of the diaper are formed, the diaper can readily deform along the body outline of the wearer owing to the presence of the thin parts. And the absorbent core shrinks in the crosswise direction to effectively prevent the expansion of the crotch region in a bag-like form. Furthermore, the thin parts formed in the crotch region elongate into regions between the thin parts in the front waist region, and in the border region between the front waist region and the crotch region, the thin parts in the front waist region and the thin parts in the crotch region are alternately arranged. Owing to the presence of the front gathering, the diaper shrinks in the crosswise direction but hardly expands forward, so that the diaper deforms into a shape adjusting to the crotch of a wearer. Through the front gathering, the diaper can fit the crotch of the wearer in such manner.

When the diaper is used in combination with a protector against incontinence, therefore, the diaper can prevent the protector from getting out of position, so that the protector can absorb urine effectively. Even when the diaper is used singly with no use of any protector against incontinence, the diaper still can retain excretion such as urine and feces securely, without causing any side leaking thereof.

Because the elastic members are arranged only at the region where the protector against incontinence is to be mounted, additionally, the remaining region can touch the skin of a wearer at the natural state, which gives pleasant feeling to the wearer when the diaper is worn.

By determining relatively the positions of the front retaining members and the back retaining members, additionally, the diaper can be made broad around the hips of a wearer and be made slim around the waist of a wearer when the diaper is worn. Thus, the diaper can be fastened securely around the waist of a wearer, whereby the positional shift of the diaper hardly occurs. Even if the diaper expands in the crotch or the hips of a wearer, the diaper can securely fasten the waist of the wearer so that the diaper can readily fit the body shape of the wearer.

What is claimed is:

1. A well-fitting disposable diaper having a front waist region to be applied to the abdominal area of a wearer, a crotch region to be applied to the crotch thereof and a back waist region to be applied to the dorsal area thereof, arranged in a longitudinal direction of the diaper in this order, comprising;

a liquid non-permeable back sheet, a liquid permeable top sheet, an absorbent core interposed between the back sheet and the top sheet and extended from the front waist region, the crotch region to the back waist region, first and second thin parts where no absorbent core is present or where the thickness of the absorbent core is reduced being formed separately in a linearly elongating fashion in the longitudinal direction, the first thin parts having intervals therebetween in a width direction perpendicular to the longitudinal direction and extending from the crotch region to the front waist region and to the back waist region, the second thin parts having intervals therebetween in the width direction and extending from the front waist region to adjacent the crotch region, and a plurality of elastic members elongating in the width direction transverse to the longitudinal direction, the elastic members being arranged in a region, which is positioned on a side of the front waist region to a center of the crotch region and includes a border between the front waist region and the crotch region, end portions of the first thin parts in the front waist region and end portions of the second thin parts adjacent the crotch region, thereby forming a front gathering, wherein the first thin part and the second thin parts alternate with each other and the first thin parts are elongated between the second thin parts, the elastic members are arranged between the absorbent core and the back sheet, the elastic members, the top sheet and the back sheet are bonded together at the thin parts, and the elastic members are arranged in such a curved fashion to protrude at the center thereof in the width direction.

2. A well-fitting disposable diaper having a front waist region to be applied to the abdominal area of a wearer, a crotch region to be applied to the crotch thereof and a back waist region to be applied to the dorsal area thereof, arranged in a longitudinal direction of the diaper in this order, comprising:

a liquid non-permeable back sheet, a liquid permeable top sheet, an absorbent core interposed between the back sheet and the top sheet, and a first retaining means and a second retaining means to be attached to each other when the diaper is applied to a wearer, the first retaining means being disposed on the back sheet in the front waist region, the first retaining means being composed of two pairs of front retaining members disposed on the back sheet with an interval therebetween in the longitudinal direction, the second retaining means being composed of two pairs of back retaining members disposed adjacent to both edges of the top sheet in the back waist region, the back retaining members in each pair having an interval therebetween in the longitudinal direction, the interval therebetween of the back retaining members in the longitudinal direction being larger than said interval therebetween of the front retaining members in the longitudinal direction, and wherein an aligning pitch of the back retaining members in each pair is larger than an aligning pitch of the front retaining members in each pair, where the aligning pitch is a distance between longitudinal centers of the retaining members in the longitudinal direction, a dimension of each of the front retaining members in the longitudinal direction is larger than a dimension of each of the back retaining members in the longitudinal direction, and the front retaining member has a rectangular shape having a larger dimension in the width direction than in the longitudinal direction.

3. The well-fitting disposable diaper according to claim 2, wherein the front retaining member is a woven fabric sheet or a non-woven fabric sheet and the back retaining member is a resin-made fastening sheet having a plurality of fastening protrusion which are to be fastened with the woven fabric sheet or the non-woven fabric sheet.

4. The well-fitting disposable diaper according to claim 2, wherein the front retaining member is a resin film and the back retaining member is an adhesive tape to be bonded to the resin film.

\* \* \* \* \*